(12) United States Patent
Choong et al.

(10) Patent No.: US 6,518,024 B2
(45) Date of Patent: Feb. 11, 2003

(54) ELECTROCHEMICAL DETECTION OF SINGLE BASE EXTENSION

(75) Inventors: Vi-En Choong, Chandler; Song Shi; George Maracas, both of Phoenix; Sean Gallagher, Scottsdale, all of AZ (US)

(73) Assignee: Motorola, Inc., Schaumburg, IL (US)

( * ) Notice: Subject to any disclaimer, the term of this patent is extended or adjusted under 35 U.S.C. 154(b) by 29 days.

(21) Appl. No.: 09/459,685

(22) Filed: Dec. 13, 1999

(65) Prior Publication Data

US 2002/0064775 A1 May 30, 2002

(51) Int. Cl.⁷ ............ C12Q 1/68; C12P 19/34; C07H 21/04
(52) U.S. Cl. ............. 435/6; 435/91.1; 435/91.2; 536/24.33
(58) Field of Search ............ 435/6, 91.1, 91.2; 536/24.33

(56) References Cited

U.S. PATENT DOCUMENTS

| | | |
|---|---|---|
| 4,656,127 A | 4/1987 | Mundy |
| 4,684,195 A | 8/1987 | Anderson et al. |
| 4,988,617 A | 1/1991 | Landegren et al. |
| 5,001,048 A | 3/1991 | Taylor et al. |
| 5,534,424 A | 7/1996 | Uhlen et al. |
| 5,547,839 A | 8/1996 | Dower et al. |
| 5,552,270 A | 9/1996 | Khrapko et al. |
| 5,591,578 A | 1/1997 | Mead et al. |
| 5,705,348 A | 1/1998 | Mead et al. |
| 5,710,028 A | 1/1998 | Eyal et al. |
| 5,741,700 A | 4/1998 | Ershov et al. |
| 5,770,369 A | 6/1998 | Mead et al. |
| 5,770,721 A | 6/1998 | Ershov et al. |
| 5,780,234 A | 7/1998 | Mead et al. |
| 5,824,473 A | 10/1998 | Meade et al. |
| 5,919,523 A | 7/1999 | Sundberg et al. |
| 5,925,520 A * | 7/1999 | Tully et al. .......... 435/6 |
| 5,952,172 A | 9/1999 | Meade et al. |
| 5,972,692 A | 10/1999 | Hashimoto et al. |
| 5,981,734 A | 11/1999 | Mirzagekov et al. |
| 6,071,699 A | 6/2000 | Meade et al. |
| 6,087,100 A | 7/2000 | Meade et al. |

FOREIGN PATENT DOCUMENTS

| | | |
|---|---|---|
| EP | 0226470 A2 | 6/1987 |
| EP | 0372911 A2 | 6/1990 |
| EP | 0543550 A1 | 5/1993 |
| EP | 0 371 437 | 2/1996 |
| EP | 0 317 074 | 12/1996 |
| WO | WO 91/13075 | 9/1991 |
| WO | WO 92/15712 | 9/1992 |
| WO | WO 96/06946 A1 | 3/1996 |
| WO | WO 97/12030 A1 | 4/1997 |
| WO | WO 98/12539 A1 | 3/1998 |
| WO | WO 98/20162 | 5/1998 |
| WO | WO 99/07879 A1 | 2/1999 |
| WO | WO 99/15893 A1 | 3/1999 |
| WO | WO 99/18242 A1 | 4/1999 |
| WO | WO 99/37819 | 7/1999 |
| WO | WO 99/57319 A1 | 11/1999 |
| WO | WO 01/06016 | 1/2001 |
| WO | W0 01/07665 A2 | 2/2001 |
| WO | WO 01/07665 | 2/2001 |

OTHER PUBLICATIONS

Pastinen et al., "Minisequencing: A Specific Tool for DNA Analysis and Diagnostics on Oligonucleotide Arrays, " Genome Research, 7:606–614 (1997).

Syvanen, A.C. "Detection of Point Mutations in Human Genes by the Solid–Phase Minisequencing Method, " Clin Chim Acta, 226(2):225–236 (1994). Abstract Only.

Yershov et al., "DNA Analysis and Diagnostics on Oligonucleotide Microchips, " Proc. Natl. Acad. Sci. 93:4913–4918 (1996).

Ihara et al., 1996, Nucleic Acids Res. 24:4273–4280.

Livache et al., 1995, Synthetic Metals 71:2143–2146.

Hasimoto, 1993, Supramolecular Chem. 2:265–270.

Millan et al., 1993, Anal. Chem. 65:2317–2323.

Syvanen, AC. ""Detection of Point Mutations In Human Genes by the Solid–Phase Minisequencing Method,"" Clin Chim Acta, 226(2):225–236 (1994). ABSTRACT ONLY.

Beattie et al., "Genosensor Technology," Clinical Chemistry, 39(4):719–722 (1993).

DiCesare et al., "A High Sensitivity Electrochemiluminescence–Based Detection System for Automated PCR Product Quantitation," BioTechniques, 15(1): 152–157 (1993).

\* cited by examiner

Primary Examiner—John S. Brusca
Assistant Examiner—Young Kim
(74) Attorney, Agent, or Firm—Dorsey & Whitney LLP; Robin M. Silva

(57) ABSTRACT

This invention relates to apparatus and methods for detecting single base extension to an oligonucleotide array using electrochemical labels.

14 Claims, 1 Drawing Sheet

ELECTROCHEMICAL DETECTION OF SINGLE BASE EXTENSION

BACKGROUND OF THE INVENTION

1. Field of the Invention

This invention relates to detection of mutated nucleic acid and genetic polymorphisms by single base extension analysis. Specifically, the invention relates to single base extension following hybridization of a biological sample comprising a nucleic acid with an oligonucleotide array. In particular, the invention provides apparatus and methods for electronic detection of single base extension of a particular oligonucleotide in an oligonucleotide array after hybridization to a nucleic acid in a biological sample and single base extension thereof.

2. Background of the Invention

The detection of single base mutations and genetic polymorphisms in nucleic acids is an important tool in modern diagnostic medicine and biological research. In addition, nucleic acid-based assays also play an important role in identifying infectious microorganisms such as bacteria and viruses, in assessing levels of both normal and defective gene expression, and in detecting and identifying mutant genes associated with disease such as oncogenes. Improvements in the speed, efficiency, economy and specificity of such assays are thus significant needs in the medical arts.

Ideally, such assays should be sensitive, specific and easily amenable to automation. Efforts to improve sensitivity in nucleic acid assays are known in the prior art. For example, the polymerase chain reaction (Mullis, U.S. Pat. No. 4,683,195, issued Jul. 28, 1987) provides the capacity to produce useful amounts (about 1 μg) of a specific nucleic acid in a sample in which the original amount of the specific nucleic acid is substantially smaller (about 1 pg). However, the prior art has been much less successful in improving specificity of nucleic acid hybridization assays.

The specificity of nucleic acid assays is determined by the extent of molecular complementary of hybridization between probe and target sequences. Although it is theoretically possible to distinguish complementary targets from one or two mismatched targets under rigorously-defined conditions, the dependence of hybridization on target/probe concentration and hybridization conditions limits the extent to which hybridization mismatch can be used to reliably detect, inter alias, mutations and genetic polymorphisms.

Detection of single base extension has been used for mutation and genetic polymorphism detection in the prior art.

U.S. Pat. No. 5,925,520 disclosed a method for detecting genetic polymorphisms using single base extension and capture groups on oligonucleotide probes using at least two types of di deoxy, chain-terminating nucleotide triphosphate, each labeled with a detectable and distinguishable fluorescent labeling group.

U.S. Pat. No. 5,710,028 disclosed a method of determining the identity of nucleotide bases at specific positions in nucleic acids of interest, using detectably-labeled chain-terminating nucleotides, each detectably and distinguishably labeled with a fluorescent labeling group.

U.S. Pat. No. 5,547,839 disclosed a method for determining the identity of nucleotide bases at specific positions in a nucleic acid of interest, using chain-terminating nucleotides comprising a photo removable protecting group.

U.S. Pat. No. 5,534,424 disclosed a method for determining the identity of nucleotide bases at specific positions in a nucleic acid of interest, using each of four aliquots of a target nucleic acid annealed to an extension primer and extended with one of four chain-terminating species, and then further extended with all four chain-extending nucleotides, whereby the identity of the nucleotide at the position of interest is identified by failure of the primer to be extended more that a single base.

U.S. Pat. No. 4,988,617 disclosed a method for determining the identity of nucleotide bases at specific positions in a nucleic acid of interest, by annealing two adjacent nucleotide primers to a target nucleic acid and providing a linking agent such as a ligase that covalently links the two oligonucleotides to produce a third, combined oligonucleotide only under circumstances wherein the two oligonucleotides are perfectly matched to the target nucleic acid at the 3' extent of the first oligonucleotide and at the 5' extent of the second oligonucleotide.

U.S. Pat. No. 4,656,127 disclosed a method for determining the identity of nucleotide bases at specific positions in a nucleic acid of interest, using primer extension with a chain-terminating or other nucleotide comprising an exonuclease-resistant linkage, followed by exonuclease treatment of the plurality of extension products to detect the resistant species therein. One common feature in this prior art is that single base extension has been detected by incorporation of fluorescent labels into the extended nucleic acid species.

A significant drawback of single base extension methods based on fluorescent label detection is the need for expensive and technically-complex optical components for detecting the fluorescent label. Although fluorescent probes used in such methods impart an adequate level of discrimination between extended and unextended positions in an oligonucleotide array, these methods typically require detection of up to four different fluorescent labels, each having a unique excitation and fluorescence emission frequency. As a consequence of these properties, such assay systems must be capable of producing and distinguishing light at all of these different excitation and emission frequencies, significantly increasing the cost and complexity of producing and operating apparatus used in the practice thereof.

An alternative method for detecting a target nucleic acid molecule is to use an electrochemical tag (or label) such as a redox moiety in combination with an electrochemical detection means such as cyclic voltammetry.

U.S. Pat. No. 5,591,578 provides for the selective covalent modification of nucleic acids with redox-active moieties such as transition metal complexes of specifically-claimed transition metals, wherein the complexes are covalently linked to a ribose sugar comprising the ribose-phosphate backbone. The resulting complexes are capable of transferring electrons over very large distances at extremely fast rates.

U.S. Pat. No. 5,705,348, related to U.S. Pat. No. 5,591,578, encompasses generally selective covalent modification of nucleic acids with redox-active moieties such as transition metal complexes, wherein the transition metals are generically-claimed.

U.S. Pat. No. 5,770,369, related to U.S. Pat. No. 5,591,578 discloses electron donor and acceptor moieties that are not redox proteins.

U.S. Pat. No. 5,780,234 369, related to U.S. Pat. No. 5,591,578, discloses methods wherein two single stranded nucleic acid are used to hybridize to two different domains of the target sequence.

In addition, disclosure of similar methods for detecting biological molecules such as DNA and proteins can be found in Ihara et al., 1996, *Nucleic Acids Res.* 24: 4273–4280; Livache et al., 1995, *Synthetic Metals* 71: 2143–2146; Hashimoto, 1993, *Supramolecular Chem.* 2: 265–270; Millan et al., 1993, Anal. Chem. 65: 2317–2323.

However, most of the electrochemical tag-dependent methods known in the prior art require hybridization of the probe/target in the presence of a redox intercalator. Electrochemical detection based on redox intercalators are generally not as reproducible as redox tags that are covalently bound to an incorporated moiety. Redox intercalator methods are exceedingly dependent on washing conditions to remove excess label while not reducing the actual signal. As a consequence, false positives are often obtained using these methods. The specificity of redox intercalator methods is often much worse than can be achieved with covalently-bound redox tags.

There remains a need in this art for simple, economical, and efficient ways to detect single base extension products of nucleic acid assays for detecting mutation and genetic polymorphisms in biological samples containing a nucleic acid of interest.

SUMMARY OF THE INVENTION

This invention provides methods and apparatus for detecting mutations and genetic polymorphisms in a biological sample containing a nucleic acid of interest. Detection of single base extension using the methods and apparatus of the invention is achieved by sequence-specific incorporation of chain-terminating nucleotide species chemically labeled with an electrochemical species. In preferred embodiments, single base extension is performed using hybridization to an oligonucleotide array, most preferably an addressable array wherein the sequence of each oligonucleotide in the array is known and associated with a particular address in the array. In additional preferred embodiments, single base extension is detected using extension products labeled with electrochemical reporter groups, wherein the electrochemical reporter groups comprise a transition metal complex, most preferably containing a transition metal ion that is ruthenium, cobalt, iron or osmium.

In the practice of the methods of the invention, the invention provides an array of oligonucleotide probes immobilized to a surface that defines a first electrode. Preferably, the sequence of each oligonucleotide at each particular identified position (or "address") in the array is known and at least one of said oligonucleotides is complementary to a sequence in a nucleic acid contained in the biological sample to be assayed (termed the "target" or "target nucleic acid"). In one preferred embodiment, the sequence of at least one oligonucleotide is selected to hybridize to a position immediately adjacent to the nucleotide position in the sample nucleic acid that is to be interrogated, i.e., for mutation or genetic polymorphism. The term "adjacent" in this context is intended to encompass positions that are one nucleotide base upstream of base to be interrogated, i.e. in the 3' direction with respect to the template strand of the target DNA. Hybridization of the oligonucleotides in the array to nucleic acid in the sample is performed in a reaction chamber and in a hybridization buffer for a time and at a temperature that permits hybridization to occur between nucleic acid in the sample and the oligonucleotides in the array complementary thereto. Single base extension is performed using a polymerase, most preferably a thermally stable polymerase, in the presence of chain-terminating primer extension units that are covalently linked to an electrochemical label. In a preferred embodiment, each chain-terminating nucleotide species (for example, di deoxy (dd)ATP, ddGTP, ddCTP and ddTTP) is labeled with a different electrochemical label, most preferably having a different, distinct and differentially-detectable reduction/oxidation potential. Single base extension is detected by applying conventional electrochemical detection methods, such as cyclic voltammetry or stipping voltammetry. Other electric or/and electrochemical methods that may also be used, include, but are not limited to, AC impedance, pulse voltammetry, square wave voltammetry, AC voltammetry (ACV), hydrodynamic modulation voltammetry, potential step method, potentiometric measurements, amperometric measurements, current step method, and combinations thereof.

In alternative embodiments, the sequence of at least one oligonucleotide is selected to hybridize to the target nucleic acid at a position whereby the 3' residue of the oligonucleotide hybridizes to the nucleotide position in the sample nucleic acid that is to be interrogated for mutation or genetic polymorphism. In the array, oligonucleotides having sequence identity to the oligonucleotide that hybridizes to the target nucleic acid at it's 3' residue will also hybridize to the target, but the 3' residue of such oligonucleotides will produce a "mismatch" with the target and will not hybridize at the 3' residue. Single base extension is performed with a polymerase that will not recognize the mismatch, so that only the oligonucleotide that hybridizes to the target including at its 3' residue will be extended. In these embodiments of the invention, only a single chain-terminating species labeled with an electrochemical species can be employed, or the same electrochemical species can be used for all four chain-terminating species, provided that the nucleotide sequence of each oligonucleotide in the array is known and properly associated with its position in the array. The detection of an electrochemical signal from the redox species using conventional electrochemical detection methods, such as cyclic voltammetry, at a particular position in the array thus provides the identity of the 3' residue of the probe and hence the identity of the complementary nucleotide at the corresponding position in the target nucleic acid.

In the practice of a preferred embodiment of the methods and use of the apparatus of the invention, electric current is recorded as a function of sweeping voltage to the first electrode specific for each particular chain-terminating nucleotide species labeled with an electrochemically-active reporter. In preferred embodiments, current flow at each specific potential is detected at each address in the array where single base extension has occurred with the corresponding chain-terminating nucleotide species labeled with a particular electrochemical reporter group. The detection of the electrical signal at a particular position in the array wherein the nucleotide sequence of the oligonucleotide occupying that position is known enables the identity of the extended nucleotide, and therefore the mutation or genetic polymorphism, to be determined.

Specific preferred embodiments of the present invention will become evident from the following more detailed description of certain preferred embodiments and the claims.

DETAILED DESCRIPTION OF THE PREFERRED EMBODIMENTS

Figure 1:
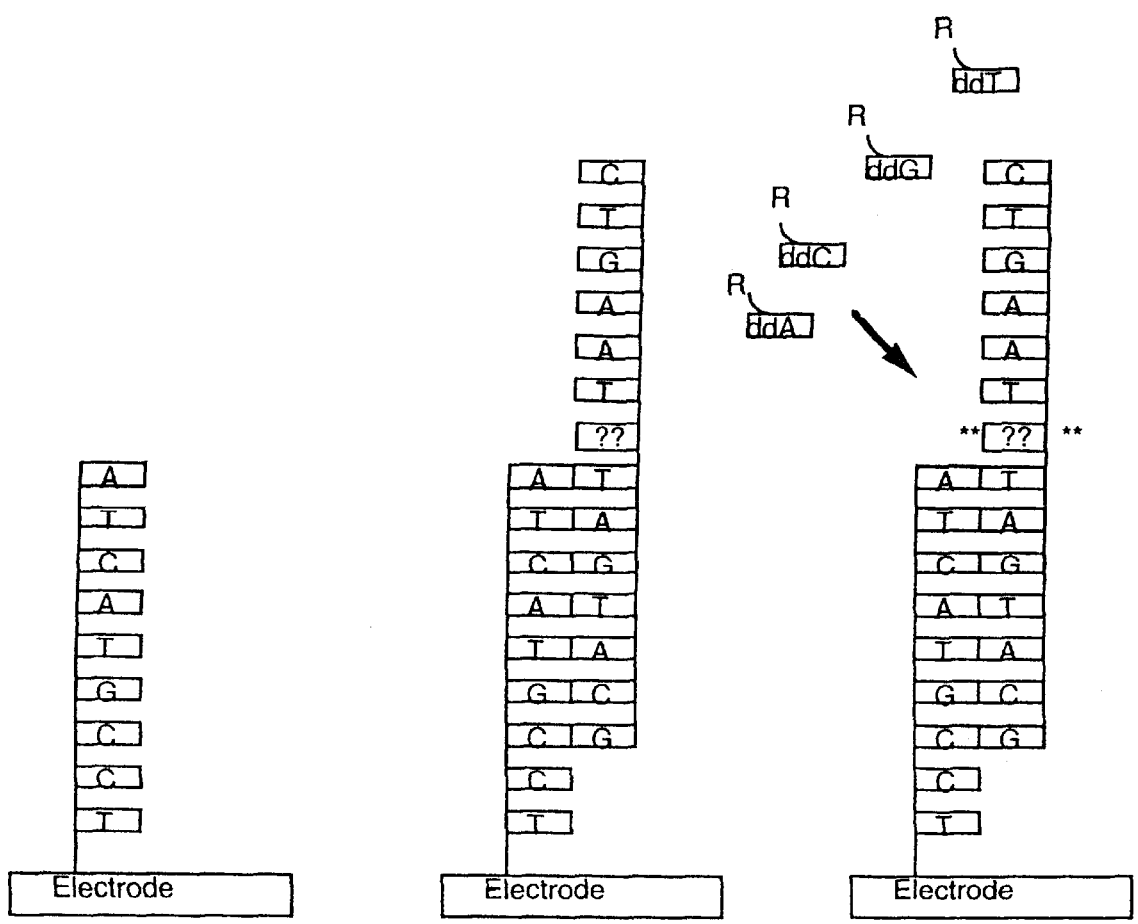
FIG. 1 illustrates single base extension using chain-terminating nucleotide species labeled with an electrochemical reporter group, according to the invention.

The present invention provides an apparatus and methods for detecting single nucleotide polymorphisms (SNP) in a nucleic acid sample comprising a specific target nucleic acid.

The devices of the invention are particularly useful for analyzing target nucleic acid for the diagnosis of infectious and genetic disease. The target nucleic acid is generally a portion of a gene having a known nucleotide sequence that is associated with an infectious agent or genetic disease; more specifically, the disease is caused by a single nucleotide (or point) mutation. The device incorporates a nucleic acid oligonucleotide array specific for the target gene, and means for detecting and detemining the identity of a specific single base in the target sequence adjacent to the hybridization site of at least one probe in the oligonucleotide array (termed the "3' offset method") or encompassing the 3' residue of at least one oligonucleotide probe in the array (termed the "3' inclusive method").

The present invention provides an array of oligonucleotide primers or probes immobilized to a surface that defines a first electrode. Preferably, the sequence of each oligonucleotide at each address in the array is known and at least one oligonucleotide in said oligonucleotide array is complementary to part of a sequence in a nucleic acid in the sample to be assayed. The sequence of at least one oligonucleotide is most preferably selected to extend to a position immediately adjacent to the nucleotide position in the sample nucleic acid that is to be interrogated, i.e., for mutation or genetic polymorphism. Alternatively, the oligonucleotide is selected to encompass the site of mutation or genetic polymorphism; in these latter embodiments, it is generally preferred to provide a multiplicity of oligonucleotides having one of each possible nucleotide at the polymorphic position to ensure hybridization of at least one of the oligonucleotides in the array to nucleic acid in the sample. Hybridization and extension reactions are performed in a reaction chamber and in a hybridization buffer for a time and at temperature that permits hybridization to occur between nucleic acid in the sample and the oligonucleotides in the array complementary thereto.

In one embodiment, the apparatus of the present invention comprises a supporting substrate, a plurality of a first electrode (or an array of microelectrodes) in contact with the supporting substrate to which probes are immobilized, at least one counter-electrode and optionally a reference electrode, and an electrolyte solution in contact with the plurality of microelectrodes, counter electrode and reference electrode.

In another embodiment, the apparatus of the present invention comprises a supporting substrate, a plurality of first electrodes (or an array of microelectrodes) in contact with the supporting substrate, a plurality of polyacrylamide gel pads in contact with the microelectrodes and to which probes are immobilized, at least one counter-electrode and optionally a reference electrode, and an electrolyte solution in contact with the plurality of microelectrodes, counter electrode and reference electrode.

In the preferred embodiment of the apparatus of the present invention, the substrate is composed of silicon. In alternative embodiments, the substrate is prepared from substances including, but not limited to, glass, plastic, rubber, fabric, or ceramics.

The electrode comprising the first surface to which the oligonucleotide or array thereof is attached is made of at least one of the following materials: metals such as gold, silver, platinum, copper, and electrically-conductive alloys thereof; conductive metal oxides such as indium oxide, indium-tin oxide, zinc oxide; and other conductive materials such carbon black, conductive epoxy.

In preferred embodiments, microelectrodes are prepared from substances including, but not limited to, metals such as gold, silver, platinum, titanium or copper, in solid or porous form and preferably as foils or films, metal oxides, metal nitrides, metal carbides, or carbon. In certain preferred embodiments, probes are attached to conjugated polymers or copolymers including, but not limited to, polypyrrole, polythiophene, polyaniline, polyfuran, polypyridine, polycarbazole, polyphenylene, poly(phenylenvinylene), polyfluorene, polyindole, their derivatives, their copolymers, and combinations thereof. In alternative embodiments, probes are attached to polyacrylamide gel pads that are in contact with the microelectrodes.

The substrate of the present invention has a surface area of between 0.01 $\mu m^2$ and 5 $cm^2$ containing between 1 and $1 \times 10^8$ microelectrodes. In one embodiment, the substrate has a surface area of 100 $\mu m^2$ and contains $10^4$ microelectrodes, each microelectrode having an oligonucleotide having a particular sequence immobilized thereto. In another embodiment, the substrate has a surface area of 100 $\mu m^2$ and contains $10^4$ microelectrodes, each microelectrode in contact with a polyacrylamide gel pad to which an oligonucleotide having a particular sequence has been immobilized thereto. In preferred embodiments, the microelectrodes are arranged on the substrate so as to be separated by a distance of between 0.05 $\mu m^2$ to 0.5 mm. Most preferably, the microelectrodes are regularly spaced on the solid substrate with a uniform spacing there between.

In one embodiment, the apparatus comprises a microarray containing at least $10^3$ microelectrodes on a single substrate to which oligonucleotide probes have been attached. Alternatively, arrayed oligonucleotides are attached to polyacrylamide gel pads that are in contact with the microelectrodes of the apparatus of the present invention. Most preferably, oligonucleotides having a particular nucleotide sequence, or groups of such oligonucleotides having related (e.g., overlapping) nucleotide sequences, are immobilized at each of the plurality of microelectrodes. In further preferred embodiments, the nucleotide sequence(s) of the immobilized oligonucleotides at each microelectrode, and the identity and correspondence between a particular microelectrode and the nucleotide sequence of the oligonucleotide immobilized thereto, are known.

The primer or probe used in the present invention is preferred to be an oligonucleotide having a length, both the upper and lower limits of which are empirically determined. The lower limit on probe length is stable hybridization: it is known in the art that probes that are too short do not form thermodynamically-stable duplexes sufficient for single base extension under the hybridization conditions of the assay. The upper limit on probe length are probes that produce a duplex in a region other than that of the predetermined interrogation target, leading to artifactual incorporation of primer extension unit(s) labeled with electrochemically active moieties. Preferred oligonucleotide plier or probes used in the present invention have a length of from about 8 to about 50, more preferably from about 10 to about 40, even more preferably from about 12 to about 30, and most preferably from about 15–25 nucleotides. However, longer probes, i.e. longer than 40 nucleotides, may also be used.

In the present invention, the primer or probe is preferably immobilized directly on the first electrode surface through an anchoring group. As will be appreciated by those in the art, advantageous anchoring groups include, for example, moieties comprising thiols, carboxylates, hydroxyls, amines, hydrazines, esters, amides, halides, vinyl groups, vinyl carboxylates, phosphates, silicon-containing organic compounds, and their derivatives. For example, an oligonucleotide which is complementary to a target DNA is covalently linked to a metallic gold electrode through a thiol-containing anchoring group. In a preferred embodiment, the length of these anchoring groups is chosen such that the conductivity of these molecules do not hinder electron transfer from the electrochemical reporter groups, to the electrode, via the hybridized probe and target DNA, and these anchoring groups in series. Stated differently, these anchoring groups are preferred to have higher conductivities than double-stranded nucleic acid. A conductivity, S, of from between about $10^{-6}$ to about $10^{-4}$ $\Omega^{-1}$ cm$^{-1}$, more preferably from about $10^{-5}$ to about $10^{3}$ $\Omega^{-1}$ cm$^{-1}$, corresponds to a length for the anchoring groups ranging from about 5 Å to about 200 Å.

Alternatively, the primer or probe can be covalently bound onto an intermediate support that is placed on top of the first electrode. The support is preferred to be either a thin layer of porous inorganic material such as TiOx, Si$_2$, NO$_x$ or a porous organic polymer such as polyacrylamide, agarose, nitrocellulose membranes, nylon, and dextran supports. Primers are covalently bound to the support through a linker. Preferred linker moieties include, but are not limited to, thioethers, ethers, esters, amides, amines, hydrazines, carboxylates, halides, hydroxyls, vinyls, vinyl carboxylates, thiols, phosphates, silicon containing organic compounds, and their derivatives and other carboxylate moieties. More preferably, biotin-streptavidin pairs are advantageous arranged to provide probe binding onto the intermediate support.

The apparatus of the invention also includes a second electrode and a reference electrode to permit current flow. The second electrode is most preferably comprised of any conducting material, including, for example, metals such as gold, silver, platinum, copper, and alloys; conductive metal oxides such as indium oxide, indium-tin oxide, zinc oxide; or other conductive materials such as carbon black, conductive epoxy; most preferred is a platinum (Pt)-wire auxiliary electrode. The reference electrode is preferably a silver wire electrode, a silver/silver chloride (Ag/AgCl) reference electrode, or a saturated calomel electrode.

The apparatus also comprises one or a multiplicity of reaction chambers, each reaction chamber being in electrochemical contact with at least one of each of the aforementioned electrodes, wherein each of the electrodes are connected to a power source and a means for controlling said power source. For the purposes of this invention, the term "in electrochemical contact" is intended to mean, inter alias, that the components are connected such that current can flow through the electrodes when a voltage potential is created between the two electrodes.

Electrochemical contact is advantageously provided using an electrolyte solution in contact with each of the electrodes or microelectrode arrays of the invention. Electrolyte solutions useful in the apparatus and methods of the invention include any electrolyte solution at physiologically-relevant relevant ionic strength (equivalent to about 0.15 SM NaCl) and neutral pH. Nonlimiting examples of electrolyte solutions useful with the apparatus and methods of the invention include but are not limited to phosphate buffered saline, HEPES buffered solutions, and sodium bicarbonate buffered solutions.

Preferred polymerases for performing single base extensions using the methods and apparatus of the invention are polymerases having little or no exonuclease activity. More preferred are polymerases that tolerate and are biosynthetically-active at temperatures greater than physiological temperatures, for example, at 50° C. or 60° C. or 70° C. or are tolerant of temperatures of at least 90° C. to about 95° C. Preferred polymerases include Taq polymerase from *T. aquaticus* (commercially available from Perkin-Elmer Centus, Foster City, Calif.), Sequenase® and ThermoSequenase® (commercially available from U.S. Biochemical, Cleveland, Ohio), and Exo(–)Pfu polymerase (commercially available from New England Biolabs, Beverley, Mass.).

The inventive methods for SNP detection provided by the invention generally comprise: (1) preparing a sample containing the target nucleic acid(s) of interest to obtain single-stranded nucleic acid that spans the specific position (typically by denaturing the sample); (2) contacting the single-stranded target nucleic acid with an oligonucleotide primer of known sequence that hybridizes with a portion of the nucleotide sequence in the target nucleic acid immediately adjacent the nucleotide base to be interrogated (thereby forming a duplex between the primer and the target such that the nucleotide base to be interrogated is the first unpaired base in the target immediately 5' of the nucleotide base annealed with the 3'-end of the primer in the duplex; this oligonucleotide is preferably a specific oligonucleotide occupying a particular address in an addressable array); (3) contacting the duplex with a reagent which includes an aqueous carrier, a polymerase, and at least one primer extension unit, wherein the primer extension unit comprises an extension moiety, an optional linker, and an electrochemical detection moiety. The primer extension reaction catalyzed by the polymerase results in incorporation of the extension moiety of the primer extension unit at the 3'-end of the primer, and the extension of the primer by a single base; (4) removing the unincorporated primer extension unit(s); and (5) determining the identity of the incorporated primer extension unit in the extended duplex by its unique electrochemical detection moiety.

The extension moiety in the primer extension unit is preferably a chain-terminating moiety, most preferably dideoxynucleoside triphosphate (ddNTPs), such as ddATP, ddCTP, ddGTP, and ddTTP; however other terminators known to those skilled in the art, such as nucleotide analogs or arabinoside triphosphate, are also within the scope of the present invention. These ddNTPs differ from conventional deoxynucleoside triphosphate (dNTPs) in that they lack a hydroxyl (group at the 3' position of the sugar component. This prevents chain extension of incorporated ddNTPs, and thus terminates the chain. Unlike conventional detection moieties that have been either fluorescent dyes or radioactive labels, the present invention provides primer extension units labeled with an electrochemical reporter group that are detected electrochemically, most preferably by redox reactions. Any electrochemically-distinctive redox label which does not interfere with the incorporation of the ddNTP into a nucleotide chain is preferred.

Optionally, the target DNA in the sample to be investigated can be amplified by means of in vitro amplification reactions, such as the polymerase chain reaction (PCR) technique well known to those skilled in the art. Enriching the target DNA in a biological sample to be used in the methods of the invention provides more rapid and more accurate template-directed synthesis by the polymerase. The use of such in vitro amplification methods, such as PCR, is optional in the methods of the invention, which feature advantageously distinguishes the instantly-disclosed methods from prior art detection techniques, which typically required such amplification in order to generate sufficient signal to be detected. Because of the increased sensitivity of the instantly-claimed methods, the extensive purification steps required after PCR and other in vitro amplification methods are unnecessary; this simplifies performance of the inventive methods.

Single base extension is performed using a polymerase in the presence of at least one primer extension unit in a buffer solution appropriate for the biochemical activity of the polymerase. A general formula of a preferred embodiment of the primer extension unit is:

ddNTP-L-R where ddNTP represents a dideoxyribonucleotide triphosphate including ddATP, ddGTP, ddCTP, ddTTP, L represents an optional linker moiety, and R represents an electrochemical reporter group, preferably an electrochemically-active moiety and most preferably a redox moiety.

In preferred embodiments, each chain-terminating nucleotide species (for example, di deoxy(dd)ATP, ddGTP, ddCTP and ddTTP) is labeled with a different electrochemical reporter group, most preferably wherein each different reporter group has a different and electrochemically-distinguishable reduction/oxidation (redox) potential. In this regard, it will be appreciated that nucleotides comprising a DNA molecule are themselves electrically active; for example, guanine and adenine can be electrochemically oxidized around 0.75 V and 1.05 V, respectively. Thus, it is generally preferable for the redox potential of the electrochemical reporter group comprising the primer extension units of the invention to be distinguishable from the intrinsic redox potential of the incorporated nucleotides themselves. The following electrochemical species are non-limiting examples of electrochemically-active moieties provided as electrochemical reporter groups of the present invention, the oxidation (+) potential or reduction (−) potential being listed in the parenthesis (in volt units):

Redox moieties useful against an aqueous saturated calomel reference electrode include 1,4-benzoquinone (−0.54 V), ferrocene (+0.307), tetracyanoquinodimethane (+0.127, −0.291), N,N,N',N'-tetramethyl-p-phenylenediamine (+0.21), tetrathiafulvalene (+0.30).

Redox moieties useful against a Ag/AgCl reference electrode include 9-aminoacridine (+0.85 V), acridine orange (+0.830), aclarubicin (+0.774), daunomycin (+0.446), doxorubicin (+0.440), pirarubicin (+0.446), ethidium bromide (+0.678), ethidium monoazide (+0.563), chlortetracycline (+0.650), tetracycline (+0.674), minocycline (+0.385), Hoechst 33258 (+0.586), Hoechst 33342 (+0.571), 7-aminoactinomycin D (+0.651), Chromomycin A, (+0.550), mithramycin A (+0.510), Vinblastine (+0.522), Rifampicin (+0.103), Os(bipyridine)$_2$(dipyridophenazine )$^{2+}$(+0.72), Co(bipyridine)$_3^{3+}$(+0.11), Fe-bleomycin (−0.08).

(The redox data are from Bard & Faullener, 1980, ELECTROCHEMICAL METHODS, John Wiley & Sons, Inc. and Hshimoto el al., 1994, *Analytica Chimica Acta.* 286: 219–224).

The choice of the electrochemically-active moiety comprising the electrochemical reporter groups of the invention is optimized for detection of the moiety to the exclusion of other redox moieties present in the solution, as well as to prevent interference of the label with hybridization between an oligonucleotide contained in an array and a nucleic acid comprising a biological sample.

The electrochemically-active moiety comprising the chain-terminating nucleotides of the invention is optionally linked to the extension nucleotide through a linker (L), preferably having a length of from about 10 to about 20 Angstroms. The linker can be an organic moiety such as a hydrocarbon chain $(CH_2)_n$, or can comprise an ether, ester, carboxyamide, or thioether moiety, or a combination thereof. The linker can also be an inorganic moiety such as siloxane (O—Si—O). The length of the linker is selected so that R, the electrochemically-active moiety, does not interfere with either nucleic acid hybridization between the bound oligonucleotide primer and target nucleic acid, or with polymerase-mediated chain extension.

In preferred embodiments, single base extension is detected by standard electrochemical means such as cyclic voltammetry (CV) or stripping voltammetry. In a non-limiting example, electric current is recorded as a function of sweeping voltage to the first electrode specific for each particular labeled primer extension unit. The incorporation and extension of a specific base is identified by the unique oxidation or reduction peak of the primer extension unit detected as current flow in the electrode at the appropriate redox potential.

In additional embodiments, other electric or/and electrochemical methods useful in the practice of the methods and apparatus of the invention include, but are not limited to, AC impedance, pulse voltammetry, square wave voltammetry, AC voltammetry (ACV), hydrodynamic modulation voltammetry, potential step method, potentiometer measurements, amperometric measurements, current step method, and combinations thereof. In all these methods, electric current is recorded as a function of sweeping voltage to the first electrode specific for each particular labeled primer extension unit. The difference is the type of input/probe signal and/or shape of input/probe signal used to sweep the voltage range. For example, in cyclic voltammetry, a DC voltage sweep is done. In ACV, an AC signal is superimposed on to the voltage sweep. In square wave voltammetry, a square wave is superimposed on to the voltage sweep. Most preferably, the signal is recorded from each position ("address") in the oligonucleotide array, so that the identity of the extended species can be determined. The identity of the nucleotide comprising the extension unit is determined from the redox potential at which current flow is detected.

In the use of the apparatus of the invention to perform a single base extension reaction, a reaction mixture is prepared containing at least one chain-terminating nucleotide labeled with an electrochemical label (such as a redox-labeled ddNTP), a hybridization buffer compatible with the polymerase and having a salt concentration sufficient to permit hybridization between the target nucleic acid and primer oligonucleotides under the conditions of the assay, and a DNA polymerase such as Taq DNA polymerase or ThermoSequenase. Single stranded target nucleic acid, for example, having been denatured by incubation at a temperature >90° C., is diluted to a concentration appropriate for hybridization in deionized water and added to the reaction mixture. The resulting hybridization mixture is sealed in a reaction chamber of the apparatus of the invention containing a first electrode, wherein the electrode comprises a multiplicity of primers having known sequence linked thereto. At least one of the primers has a nucleotide sequence capable of hybridizing with a portion of the nucleotide sequence of the target immediately adjacent the nucleotide base to be interrogated under the hybridization conditions employed in the assay.

A duplex between the primer and the target is formed wherein the nucleotide base to be interrogated is the first unpaired base in the target immediately 5' of the nucleotide base that is annealed with the 3'-end of the primer in the duplex. Single base extension of the 3' end of the annealed primer is achieved by incorporation of the chain-terminating nucleotide, labeled with an electrochemically active moiety, into the primer. The primer sequence and labeled chain-terminating nucleotide are chosen so that incorporation of the nucleotide is informative of the identity (i.e., mutant, wildtype or polymorphism) of the interrogated nucleotide in the target.

Alternatively, the probe comprises a 3' terminal residue that corresponds to and hybridizes with the interrogated base. In these embodiments, oligonucleotides having a "mismatch" at the 3' terminal residue will hybridize but will not be extended by the polymerase. Detection of incorporation of the primer extension unit by interrogating the redox label is then informative of the identity of the interrogated nucleotide base, provided that the sequence of the oligonucleotide probe is known at each position in the array.

After the SBE reaction is performed, the electrode is washed at high stringency (i.e., in a low-salt and low dielectric constant solution (such as 0.1×SSC: 0.015 M NaCl, 15 mM sodium citrate, pH 7.0), optionally including a detergent such as sodium dodecyl sulfate at temperature of between about 10–65° C.) for a time and at a temperature wherein the target nucleic acid is removed. Wash conditions vary depending on factors such as probe length and probe complexity. Electrochemical detection is carried out in an electrolyte solution by conventional cyclic voltammetry.

EXAMPLE 1

An apparatus of the invention is produced as follows. A glass substrate layer is prepared comprising an ordered array of a plurality of gold microelectrodes connected to a voltage source. The substrate has a surface area of 100 $\mu m^2$ and contains $10^4$ microelectrodes, each microelectrode in contact with a polyacrylamide gel pad that is about 0.5 $\mu m$ thick to which an oligonucleotide having a particular sequence has been immobilized thereto. The microelectrodes are arranged on the substrate so as to be separated by a distance of about 0.1 $\mu m$, and are riegularly spaced on the solid substrate with a uniform spacing there between.

To each of the gold electrodes is affixed an oligonucleotide probe having a length of 25 nucleotides. The resulting ordered array of probes are arranged in groups of four, whereby the probes are identical except for the last (most 3') residue. Each group contains an oligonucleotide ending in an adenosine (A), guanine (G), cytosine (C) or thymidine (T) or uracil (U) residue. The oligonucleotides are attached to each of the gold electrodes through the polyacrylamide gel pad using a modification of the oligonucleotide at the 5' residue. This residue comprises a thioester linkage that covalently attaches the oligonucleotide to the polyacrylamide polymer.

This ordered microelectrode array is placed in a reaction chamber, having dimensions sufficient to contain the array and a volume of from about 10 to 100 $\mu L$ of hybridization/extension buffer. The reaction chamber also comprises a second counter electrode comprising platinum wire and a third, reference electrode that is a silver/ silver chloride electrode, each electrode being electrically connected to a voltage source.

In the use of the apparatus of the invention, a volume of from about 10 to 100 $\mu L$ of hybridization buffer is added to the reaction chamber. This solution also contains a target molecule, typically at concentrations in the micromolar ($10^{-6}$ M; $\mu M$) to attomolar ($10^{-18}$ M; aM) range. Hybridization of probe and target molecules is performed in 1×SSC buffer (0.15 M NaCl, 0.015 M sodium citrate, pH 7.0) at 37° C. for 24 to 48 hours. Following hybridization, microelectrodes were thoroughly rinsed in an excess volume of 1×SSC at room temperature.

A volume of from about 10 to 100 $\mu L$ of extension buffer containing a polymerase and a plurality of each of 4 chain-terminating nucleotide species is then added to the reaction chamber. Each of the four chain-terminating nucleotide species is labeled with a chemical species capable of participating in a reduction/oxidation (redox) reaction at the surface of the microelectrode. An example of such a collection of species is: ddATP labeled with cobalt (bipyridine)$_3^{3+}$; ddGTP labeled with minocycline; ddCTP labeled with acridine orange; and ddTTP labeled with ethidium monoazide. The redox labels are covalently linked to the chain-terminating nucleotides by a hydrocarbon linker $(CH_2)_{2-8}$. The extension buffer is chosen to accommodate the polymerase, such as ThermoSequenase (obtained from U.S. Biochemicals, Cleveland, Ohio). The extension reaction is performed at a temperature appropriate for the polymerase, such as about 65° C., that does not denature the hybridized duplex between the target and the oligonucleotide probes, and for a time sufficient for the extension reaction to go to completion. After the extension reaction is complete, the array is washed at high stringency in 0.1×SSC/ 1% SDS at a temperature that does not denature the hybridized duplex.

After washing, a volume of about 10 to 100 $\mu L$ of an electrolyte solution is added to the reaction chamber, and each microelectrode is interrogated by conventional cyclic voltammetry to detect a redox signal. The identity of oligonucleotides containing single base extended species is determined by the redox potential of the signal obtained thereby.

Equivalently, hybridization and single base extension can be performed in the same buffer solution, provided the polymerase is compatible with the hybridization buffer conditions.

It should be understood that the foregoing disclosure emphasizes certain specific embodiments of the invention and that all modifications or alternatives equivalent thereto are within the spirit and scope of the invention as set forth in the appended claims.

What we claimed is:

1. A method for identifying a base at an interrogation position in a target sequence of a sample, said method comprising:
   a) contacting said sample with an oligonucleotide array comprising a plurality of microelectrodes each comprising a polyacrylamide gel pad and a different immobilized oligonucleotide probe, under conditions whereby said target sequence hybridizes to at least one of said oligonucleotide probes at a position adjacent to said interrogation position to form a hybridization complex;
   b) contacting said hybridization complex with a hybridization solution comprising:
      i) a polymerase; and
      ii) different primer extension units each comprising a chain-terminating nucleotide and a different electrochemical reporter group; under conditions whereby a primer extension unit is added to the terminus of said probe in said hybridization complex; and
   c) detecting the presence of said electrochemical reporter group to identify the base at said interrogation position.

2. A method according to claim 1 wherein at least one of said electrochemical reporter groups is ferrocene.

3. A method according to claim 1 wherein at least one of said electrochemical reporter groups comprises transition metal complex.

4. A method according to claim 3 wherein said transition metal complex comprises a transition metal ion selected from the group consisting of ruthenium, iron, cobalt and osmium.

5. A method according to claim 1 wherein said chain-terminating nucleotides are dideoxyribonucleotides.

6. A method according to claim 1 wherein said chain-terminating nucleotides are acyclonucleotides.

7. A method according to claim 1 wherein said electrochemical reporter groups are covalently linked to said chain-terminating nucleotides using a linker moiety.

8. A kit used for identifying a base at an interrogation position in a target sequence of a sample, said kit comprising:
   a) an apparatus comprising:
      i) an oligonucleotide array comprising a plurality of microelectrodes each comprising a polyacrylamide gel pad and a different immobilized oligonucleotide probe,
      ii) a voltage source and
      iii) a detector to detect the presence of an electrochemical reporter label;
   b) a hybridizing solution comprising:
      i) chain-terminating nucleotides labeled with different electrochemical reporters, and
      ii) a polymerase.

9. A kit according to claim 8 wherein at least one of said electrochemincal reporter groups is ferrocene.

10. A kit according to claim 8 wherein at least one of said electrochemical reporter groups comprises a transition metal complex.

11. A kit according to claim 10 wherein said transition metal complex comprises a transition metal ion selected from the group consisting of ruthenium, iron, cobalt and osmium.

12. A kit according to claim 8 wherein said chain-terminating nucleotides are dideoxyribonucleotides.

13. A kit according to claim 8 wherein said chain-terminating nucleotides are acyclonucleotides.

14. A kit according to claim 8 wherein said electrochemical reporter groups are covalently linked to said chain-terminating nucleotides using a linker moiety.

* * * * *

UNITED STATES PATENT AND TRADEMARK OFFICE
CERTIFICATE OF CORRECTION

PATENT NO.     : 6,518,024 B2                                Page 1 of 1
DATED          : February 11, 2003
INVENTOR(S)    : Vi-En Choong et al.

It is certified that error appears in the above-identified patent and that said Letters Patent is hereby corrected as shown below:

Title page,
Item [56], References Cited, U.S. PATENT DOCUMENTS, change the spelling of "Mead" in four instances to -- Meade --.
FOREIGN PATENT DOCUMENTS, add -- WO 98/54294 12/1998 --.

Column 1,
Line 46, change "inter alias" to -- inter alia --;
Line 54, change "di deoxy" to -- dideoxy --; and
Line 65, change "photo removable" to -- photoremovable --.

Column 4,
Lines 1 and 2, change "di deoxy (dd)ATP" to -- dideoxy(dd)ATP --.

Column 6,
Line 53, change "plier" to -- primer --.

Column 8,
Line 44, change "(group" to -- group --.

Column 9,
Line 18, change "di deoxy(dd)ATP" to -- dideoxy(dd)ATP --.

Signed and Sealed this

Eighteenth Day of November, 2003

JAMES E. ROGAN
*Director of the United States Patent and Trademark Office*